(12) United States Patent
Dornberger et al.

(10) Patent No.: US 10,578,459 B2
(45) Date of Patent: Mar. 3, 2020

(54) METHOD FOR OPERATING AN X-RAY DEVICE

(71) Applicants: Susanne Dornberger, Erlangen (DE); Dominikus Joachim Müller, Eichenau (DE); Verena Schmidt, Erbendorf (DE); Stefan Schwarzer, Taufkirchen (DE)

(72) Inventors: Susanne Dornberger, Erlangen (DE); Dominikus Joachim Müller, Eichenau (DE); Verena Schmidt, Erbendorf (DE); Stefan Schwarzer, Taufkirchen (DE)

(73) Assignee: Siemens Healthcare GmbH, Erlangen (DE)

( * ) Notice: Subject to any disclaimer, the term of this patent is extended or adjusted under 35 U.S.C. 154(b) by 237 days.

(21) Appl. No.: 15/496,593

(22) Filed: Apr. 25, 2017

(65) Prior Publication Data

US 2017/0307410 A1 Oct. 26, 2017

(30) Foreign Application Priority Data

Apr. 26, 2016 (DE) .................. 10 2016 207 021

(51) Int. Cl.
| | | |
|---|---|---|
| *G01T 7/00* | (2006.01) | |
| *G01D 5/20* | (2006.01) | |
| *A61B 6/00* | (2006.01) | |
| *G01N 23/04* | (2018.01) | |

(52) U.S. Cl.
CPC .............. *G01D 5/20* (2013.01); *A61B 6/547* (2013.01); *G01N 23/04* (2013.01); *G01N 2223/34* (2013.01); *G01T 7/005* (2013.01)

(58) Field of Classification Search
CPC .......... G01D 5/20; A61B 6/547; G01N 23/04; G01N 2223/34; G01T 7/005
See application file for complete search history.

(56) References Cited

U.S. PATENT DOCUMENTS

| | | |
|---|---|---|
| 5,463,669 A | 10/1995 | Kaplan |
| 2007/0001905 A1 | 1/2007 | Eronen |
| 2014/0247918 A1 | 9/2014 | Kang et al. |

(Continued)

FOREIGN PATENT DOCUMENTS

| | | |
|---|---|---|
| DE | 102010020782 A1 | 11/2011 |
| EP | 2774541 A1 | 9/2014 |
| WO | WO2012127117 A1 | 9/2012 |

OTHER PUBLICATIONS

European Search Report for related European Application No. 17167096.1 dated Aug. 17, 2017.

(Continued)

*Primary Examiner* — Courtney D Thomas
(74) *Attorney, Agent, or Firm* — Lempia Summerfield Katz LLC

(57) ABSTRACT

A method and device for operating an x-ray device including an x-ray emitter and an x-ray detector are provided. An alternating magnetic field is produced and emitted at the x-ray emitter. At least two sensors are included for capturing at least one physical variable correlating with the alternating magnetic field. An alignment of the x-ray detector relative to the x-ray emitter is determined based on the measurement.

9 Claims, 4 Drawing Sheets

(56) References Cited

U.S. PATENT DOCUMENTS

| | | | | |
|---|---|---|---|---|
| 2014/0376700 A1* | 12/2014 | Kwak | ................... | A61B 6/4291 |
| | | | | 378/205 |
| 2015/0049863 A1* | 2/2015 | Stagnitto | .............. | A61B 6/4291 |
| | | | | 378/205 |
| 2015/0137801 A1* | 5/2015 | Raedy | ..................... | H02J 5/005 |
| | | | | 324/207.15 |

OTHER PUBLICATIONS

German Office Action for related German Application No. 10 2016 207 021.5 dated Apr. 25, 2017, with English Translation.

* cited by examiner

Configuration for x-displacement

Configuration for y-displacement

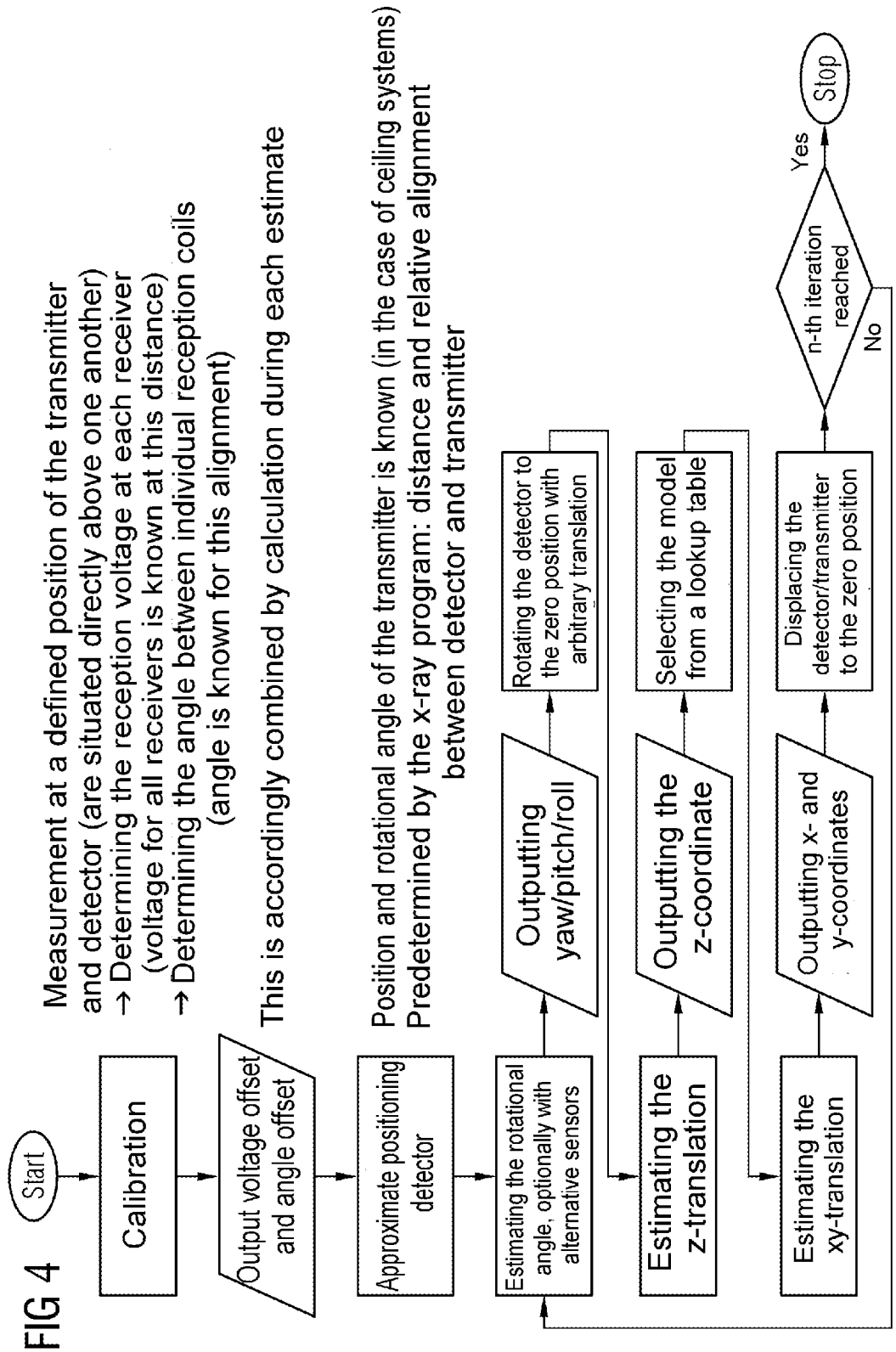

METHOD FOR OPERATING AN X-RAY DEVICE

CROSS REFERENCE TO RELATED APPLICATION

This application claims the benefit of DE 102016207021.5 filed on Apr. 26, 2016, which is hereby incorporated by reference in its entirety.

FIELD

Embodiments relate to systems and methods for operating an x-ray device.

BACKGROUND

Information about the relative orientation and position between emitter and detector of an x-ray device is used for obtaining a defined x-ray image by the x-ray device, for example, by the arrangement consisting of an x-ray emitter and an x-ray detector.

Orientation encompasses a translational displacement of the detector relative to the emitter and a tilt/twist of the detector relative to the emitter, in each case in all three spatial axes that may be referred to as roll-pitch-yaw angle, the latter constituting a possibility for describing the orientation of an object in three-dimensional space.

Current devices do not provide the information in respect of the relative orientation and position of an x-ray detector in relation to the associated x-ray emitter.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a solution that facilitates a reliable determination of the orientation.

In an embodiment, a method is provided for operating an x-ray device including a x-ray emitter and a x-ray detector. An alternating magnetic field is produced and emitted at the x-ray emitter. At least two sensors attached for respectively capturing at least one physical variable, in particular the magnetic field strength, correlating with the alternating magnetic field are used at the x-ray detector to carry out a measurement of the physical variables. An alignment of the x-ray detector relative to the x-ray emitter is determined on the basis of the measurement.

Embodiments provide automating the alignment that was previously carried out manually and that is defined within by the orientation of the detector in relation to the emitter, at which the distance between x-ray emitter and x-ray detector was measured, in part using a tape measure. In relation thereto, embodiments also provide more precise determinations of the orientation. A tilt of the detector may not be ascertained by metrology, but only corrected using a "visual estimation". Errors are avoided during the x-ray recording that leads to, for example, the x-ray image either having a poor quality (field of view, unsharpness, low contrast) or having to be repeated, meaning additional radiation exposure.

In an embodiment, a translation and/or rotation is calculated at least in a plane in each case for the determination purposes.

Various mathematical algorithms may be selected or used in a targeted manner for an accurate estimate of the orientation depending on the number of planes and the type of ascertained orientation offset—both translationally and/or rotationally.

Simple ascertaining/estimating of the translation (translation offset) may be implemented if at least two transmitters for emitting the alternating magnetic field are operated in a manner arranged symmetrically with respect to one another and/or if the at least two sensors are operated in a manner arranged symmetrically with respect to one another, where the measurement is carried out in such a way that a ratio is formed of the physical variable, in particular the reception field strength, as received on the part of the sensors and wherein the determination is carried out on the basis of this ratio. However, the ascertainment/estimate may only be applicable to the extent that there may not be a tilt (tip)/twist possibility of the detector. As a result, a pure gradient method is provided.

In order to render a determination possible even in the case of a tilt/twist, the method may provide that at least four sensors are operated arranged on the x-ray detector. The correlation is carried out such that a position estimate is ascertained by relating physical variables received at the current time to a reference variable. The determination is carried out on the basis of the position estimate. A determination approach may be used that may be referred to as a spherical model.

Alternatively, for example, if no translation offset is possible, or in a complementary manner, at least one pair of sensors are operated arranged orthogonal with respect to one another on the x-ray detector. The measurement is carried out so that the angle of incidence is ascertained on the basis of the received physical variables between the two sensors by applying trigonometric functions, for example, the arctangent. The determination is carried out on the basis of the angle of incidence. As a result of ascertaining the rotation, i.e., an offset of the rotation in relation to the emitter is determined on the basis of a trigonometric function, for example, the arctangent.

The accuracy of ascertaining the offset of the rotation may be increased further if more than one pair of sensors is used. An angle of incidence is determined for each pair, a mean value is formed from the angles of incidence of the pairs, and the determination is carried out on the basis of the mean value of the angle of incidence.

The alternating field may be produced in such a way in the process that the magnetic field has a frequency in a range between 75 kHz and 150 kHz, for example 125 kHz. As a result, a frequency range, that is suited to penetrate the materials and the human body virtually without the bothersome influences, is implemented. 125 kHz, for example, may be predetermined by regulators.

If one-dimensional, two-dimensional and/or three-dimensional coils are operated as transmitters, the determination becomes more accurate.

In an embodiment, reception coils, 3-axis acceleration sensors and/or 3-axis rotational speed sensors are operated as sensors. Various degrees of freedom are obtained for the implementation as each of the sensor types is accompanied by properties that may be of particular advantage for a specific use.

The x-ray device in an embodiment includes an x-ray emitter and an x-ray detector. The x-ray emitter is configured with transmitters for producing and transmitting an alternating magnetic field. The x-ray detector is configured with at least two sensors for respectively capturing at least one physical variable, for example, the magnetic field strength, correlating with the alternating magnetic field. The x-ray device carries out a correlation of the physical variables. The x-ray device may be configured in such a way that an alignment of the x-ray detector relative to the x-ray emitter is determined on the basis of the measurement.

BRIEF DESCRIPTION OF THE FIGURES

FIG. 4 depicts a flowchart of an embodiment of operating an x-ray device.

DETAILED DESCRIPTION

Figure 1:
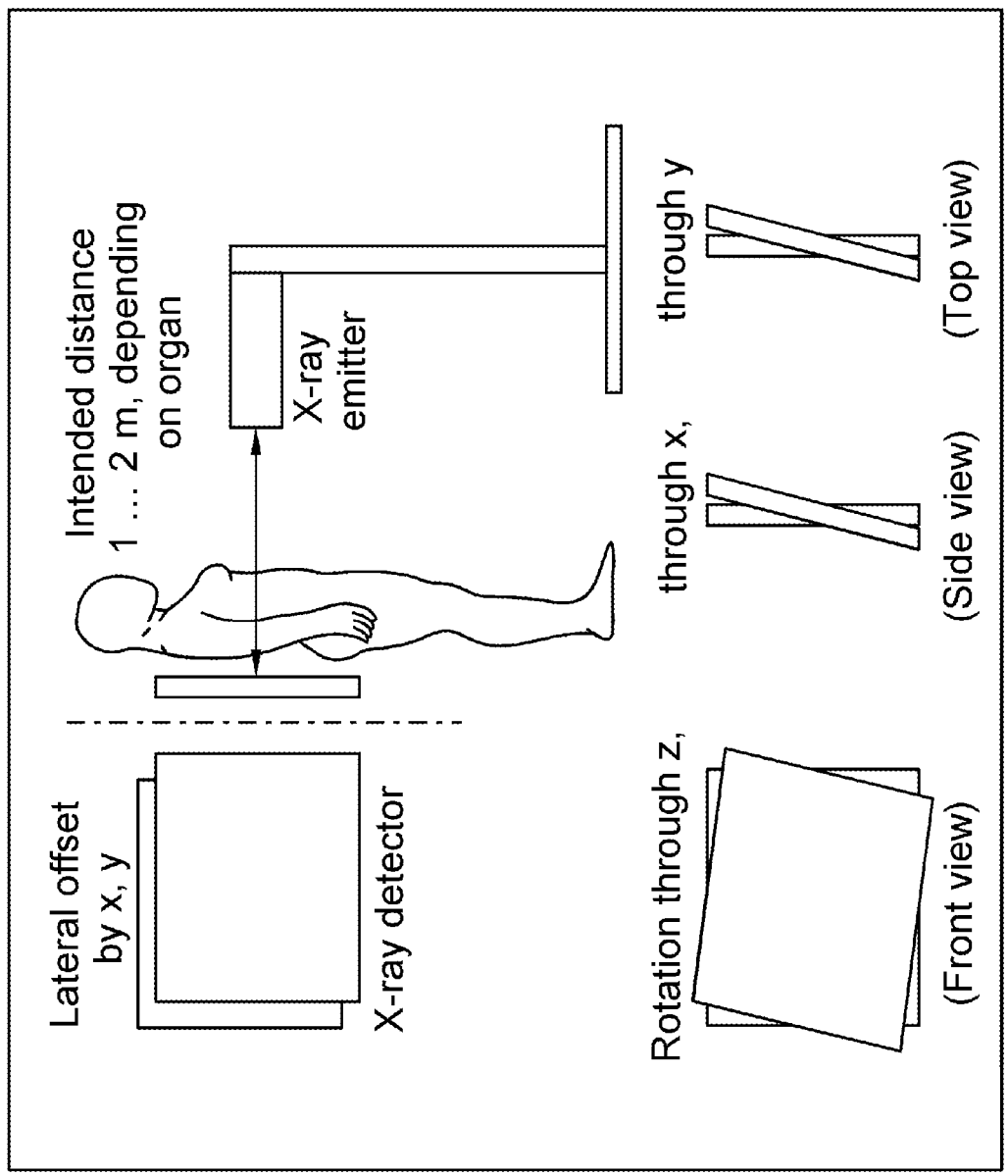
FIG. 1 depicts an x-ray device arrangement in accordance with the prior art.

FIG. 1 depicts, in a simplified manner, an x-ray device arrangement.

The x-ray device arrangement includes an emitter (e.g., an x-ray emitter) and a detector (e.g., an x-ray detector), between which a person to be examined is placed.

Depicted further is the way in which the orientation of the x-ray detector may change such that the x-ray detector has an offset in relation to the emitter that is immovable.

There may be a displacement of the detector in the xy-plane (e.g., a translation offset). The detector may also be effected such that the detector is rotated about one of the three xyz axes in space.

The orientation of the detector emerging may be determined manually and leads to disadvantages.

In an embodiment, the disadvantages are rectified by providing an automated capture of the offset.

Figure 2:
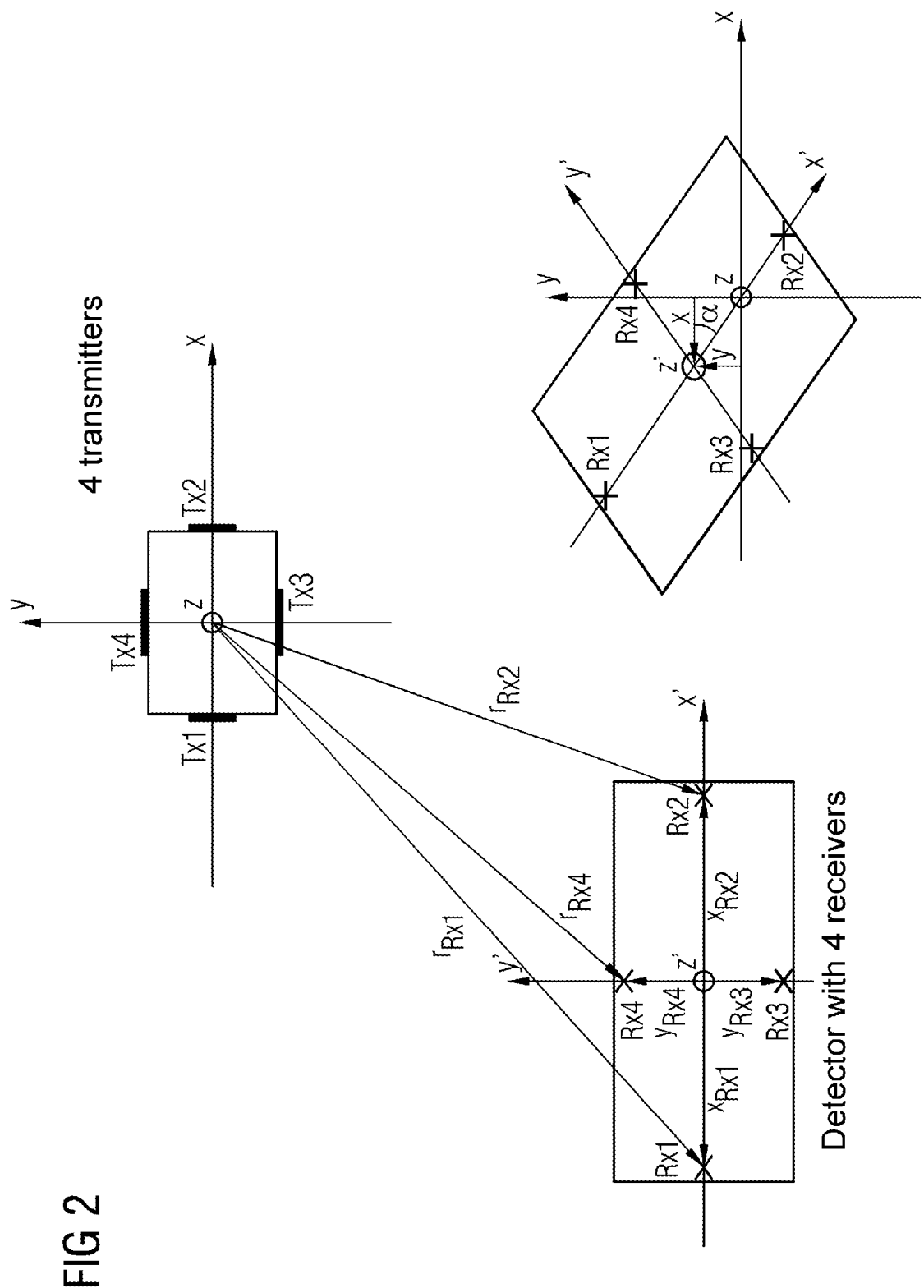
FIG. 2 depicts an embodiment that highlights the application according to a spherical model as a measurement principle.

The embodiment in FIG. 2 depicts the use of transmitters (denoted by the lines on the edge of the emitter) Tx1 . . . Tx4, that are placed on the emitter, and the use of receivers (symbolically depicted by "x" at the edge of the detector) Rx1 . . . Rx4. As depicted, the placement may be symmetric among the transmitters/receivers with respect to one another and may also be configured such that, for example, the receivers are attached orthogonally with respect to one another. Alternatively, use may also be made of more than 4 receivers Rx1 . . . Rx4.

The rotational angle and the position for the conceivable offset possibilities may be determined.

The transmitters produce an alternating magnetic field and the receivers are configured as coils. The received voltages are ascertained by at least two orthogonal reception coils. The angle of incidence between the two reception coils may be determined with the aid of the arctangent trigonometric function if linearly emitted magnetic fields are assumed. The mean value of the estimated rotational angle is determined in the case of a plurality of reception coil pairs. The orientation may be determined in general by trigonometric functions if three reception coils are used (e.g., there is no restriction to the arctangent). The accuracy of the estimate is dependent on: a homogeneous field distribution produced by the transmission coils, orthogonality of the reception coils (e.g., coupling, installation), and the signal-to-noise ratio.

A tilt or rotation in space (e.g., yaw, pitch, roll) about one axis only may be measured via two reception coils (Rx1, Rx2) that are crossed by 90°. The installation locations are on the main axes of the detector. Yaw reception coils lie in the x'y'-plane. Pitch reception coils lie in the x'z'-plane. Roll reception coils lie in the y'z'-plane. The estimated angle=a tan(measurement at Rx1/measurement at Rx2). In an embodiment, a 3D reception coil is used to capture a tilt about two axes. There is a calibration of the reception coils prior to an angle estimate.

An angle measurement using a trigonometric function may only be applicable in the case of a homogeneous phase in space.

The position of the detector in the given initial situation may be ascertained by the use of measurement principles, for example, a spherical model and a gradient model/gradient method. The spherical model includes estimating the position of the detector relative to the transmitter using a spherical model. The depicted four receivers are used for estimating the x, y, z position of the detector. The spherical model is based on an empirical model. The empirical model is based on measurements of the field strengths that are ascertained once in the case of relevant distances between transmitter and detector and in a relevant region in the case of a constant distance. A cost function for each receiver is minimized for each measured value.

The following equations describing/modeling the conditions of the x-ray arrangement are used in the spherical model:

$$r_{Rx1} = \sqrt{(x+x_1)^2 + (y+y_1)_2 + (z+z_1)^2}$$

$$r_{Rx2} = \sqrt{(x+x_2)^2 + (y+y_2)_2 + (z+z_2)^2}$$

$$r_{Rx3} = \sqrt{(x+x_3)^2 + (y+y_3)_2 + (z+z_3)^2}$$

$$r_{Rx4} = \sqrt{(x+x_4)^2 + (y+y_4)_2 + (z+z_4)^2}$$

The model equations for the four receivers are provided herewith. The Euler matrix M with $$\begin{pmatrix} x_n \\ y_n \\ z_n \end{pmatrix} = M \cdot \begin{pmatrix} x_{Rxn} \\ y_{Rxn} \\ z_{Rxn} \end{pmatrix}$$

is provided for a receiver with an offset from the center point of the detector and with xn, yn, zn, depending on the spatial angles yaw α, roll β, and pitch γ. In the case of a rotation about the z-axis, as depicted in the figure (with a value of the angle α=45°), the matrix would emerge as follows from which the rotational angle may be determined.

$$M = \begin{pmatrix} \cos\alpha & -\sin\alpha & 0 \\ \sin\alpha & \cos\alpha & 0 \\ 0 & 0 & 1 \end{pmatrix}$$

The position (e.g., the displacement in accordance with the illustration by x=y=10 cm) of the detector from the center point with respect to all transmitters Txn is estimated from the reception voltages at all receivers Rxn.

For estimating the xy-translation by the spherical equation, the xy estimate is based on a polynomial. For the polynomial, the field distribution is not symmetrical, a polynomial determines the mean value of all curves, a radius is assigned with the aid of the polynomial of each measured reception voltage, and at least three reception coils are therefore sufficient for the estimation (e.g., because or if the z-distance is constant and known). An estimation error is minimized if further receivers are used. If the polynomials are used for the estimation, the error is suitable for relatively small displacements as measurement errors increase with increasingly large displacements. The estimation principle is also applicable for a rotation of the detector. The mean Euclidean distance may be 1.7 cm.

The accuracy achieved by one-dimensional reception coils is sufficient and offers an expedient solution. More accurate results may also be obtained by the use of two-dimensional or three-dimensional coils.

Figure 3:
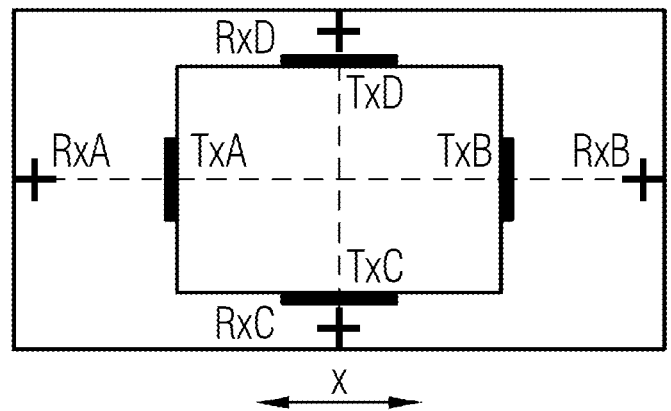
FIG. 3 depicts schematically an embodiment including a gradient model as a measurement principle.
Figure 3:
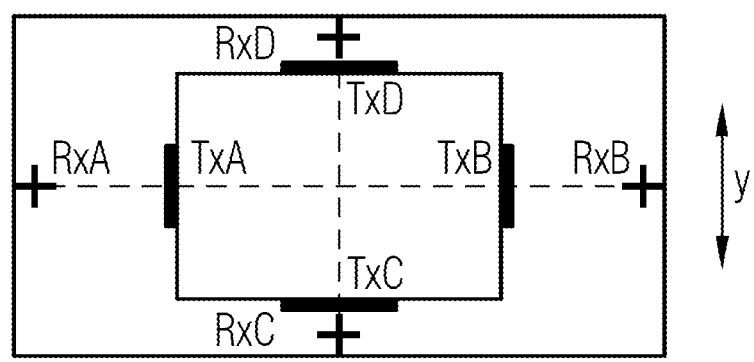

By contrast, the gradient method, as depicted in FIG. 3, indicated on the basis of an initial situation (e.g., a purely translational displacement) includes where the xy-displacement is determined by a gradient. The displacement may be determined via a reception ratio of a symmetrical transmission and reception configuration. The displacement is applicable if no rotation/tilt is present. The gradient may be valid for a distance. The principle that a displacement is present if two opposing receivers do not detect the same reception field strength is used. The mean Euclidean distance may be 0.3 cm.

Further, a suitable polynomial may be determined for the estimation in accordance with an embodiment, taking into account the following points.

The measured reception voltages depend on the position of the reception coils on the detector (e.g., Rx1 and Rx2 have a greater distance from the detector center than Rx3 and Rx4).

For a rough estimate of the distance, a polynomial that is based on the addition of the voltages from all reception coils is determined.

For estimating the distance accurately, a polynomial emerging from the voltages from reception coils having an identical distance from the center of the detector may be determined.

The corresponding polynomial is assigned to each reception coil depending on the position thereof on the detector plate. The assignment provides a good correlation of radii to reception voltages at various distances.

Since a spherical equation may also be established by a polynomial for each receiver in accordance with an alternative embodiment, there may also be an estimate by the spherical model, where the z-component may be estimated very well if the estimated x- and y-components correspond to 0.

FIG. 4 depicts a flowchart of an embodiment. At act S1, an initial state "start" is followed by a calibration in act S2. The calibration ascertains a voltage and angle offset as a result in act S3 by virtue of a measurement carried out at a defined position of the transmitter and of the detector (e.g., such that the transmitter and detector are situated directly over one another. The reception voltage at each receiver and angles between the individual reception coils are determined.

Approximate positioning is then carried out in act S4. At act S5, the rotational angle is estimated.

At act S6, the spatial angles yaw/pitch/roll are output. At step S7, the detector is rotated to the zero position (e.g., with any translation).

The z-translation is estimated at act S8. The z-coordinate is outputted at act S9. A model is selected at act S10. The model is used in act S11 to estimate the xy-translation and carry out a displacement of the detector/transmitter to the zero position in act S12.

An evaluation is carried out at act S13 as to whether n-iterations have been reached. The method is completed in the affirmative and proceeds to the "stop" state in at act S14.

If n-iterations have not been reached, acts S5 . . . S11 are repeated.

The approach described in this document is not restricted to the examples explained. For example, the orientation of objects in space and the position thereof are accomplished with the aid of a selection of sensors, homogeneous in respect of type, from a selection, possible in principle, of a plurality of sensor types (e.g., acceleration sensor, gyro, etc.) that are used in a comparable way to the orientation control of aircraft, which is not in the art.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an x-ray device comprising an x-ray emitter and an x-ray detector, the method comprising:
    generating and emitting an alternating magnetic field by at least two transmitters positioned on the x-ray emitter and arranged symmetrically with respect to one another;
    measuring a magnetic field strength that correlates with the alternating magnetic field by each sensor of a plurality of sensors positioned on the x-ray detector, wherein the plurality of sensors comprises a first pair of sensors arranged symmetrically with respect to one another and a second pair of sensors arranged symmetrically with respect to one another;
    ascertaining an angle of incidence for each pair of sensors based on the measured magnetic field strengths between each pair of sensors, wherein the ascertaining comprises applying trigonometric functions;
    calculating a mean value from the ascertained angle of incidence of each pair of sensors;
    determining a rotation of the x-ray detector about at least two axes relative to the x-ray emitter based on the calculated mean value for each pair of sensors; and
    determining a three-dimensional position of the x-ray detector relative to the x-ray emitter based on the magnetic field strength measurements by the plurality of sensors.

2. The method of claim 1,
    wherein the measuring comprises ascertaining a position estimate, the ascertaining comprising relating physical variables received at a current time to a reference variable, and
    wherein the determining is based on the position estimate.

3. The method of claim 1, wherein the trigonometric functions include an arctangent.

4. The method of claim 1, wherein the alternating magnetic field is generated with a frequency in a range between 75 kHz and 150 kHz.

5. The method of claim 4, wherein the alternating magnetic field is generated with a frequency of 125 kHz.

6. The method of claim 1, wherein the at least two transmitters include one-dimensional coils, two-dimensional coils, three-dimensional coils, or any combination thereof.

7. The method of claim 1, wherein the plurality of sensors comprise 3-axis acceleration sensors, 3-axis rotational speed sensors, or both the 3-axis acceleration sensors and the 3-axis rotational speed sensors.

8. An x-ray device comprising:
   an x-ray emitter comprising at least two transmitters arranged symmetrically with respect to one another, wherein the at least two transmitters are configured to produce and transmit an alternating magnetic field; and
   an x-ray detector comprising a plurality of sensors, the plurality of sensors having a first pair of sensors arranged symmetrically with respect to one another and a second pair of sensors arranged symmetrically with respect to one another, wherein each sensor of the plurality of sensors is configured to measure a magnetic field strength correlating with the alternating magnetic field,
   wherein the x-ray device is configured to:
      ascertain an angle of incidence for each pair of sensors based on the measured magnetic field strengths between each pair of sensors, wherein the ascertaining comprises applying trigonometric functions;
      calculate a mean value from the ascertained angle of incidence of each pair of sensors;
      determine a rotation of the x-ray detector about at least two axes relative to the x-ray emitter based on the calculated mean value for each pair of sensors; and
      determine a three-dimensional position of the x-ray detector relative to the x-ray emitter based on the magnetic field strength measurements by the plurality of sensors.

9. The x-ray device of claim 8,
   wherein the measurement comprises ascertainment of a position estimate, the ascertainment comprising relation of physical variables received at a current time to a reference variable, and
   wherein the determination of the rotation of the x-ray detector is based on the position estimate.

* * * * *